United States Patent [19]

Ebert et al.

[11] Patent Number: 4,532,126
[45] Date of Patent: Jul. 30, 1985

[54] MASTICATORY SOFT ELASTIC GELATIN CAPSULES AND METHOD FOR THE MANUFACTURE THEREOF

[75] Inventors: William R. Ebert; Foo S. Hom; Warren W. Kindt, all of Clearwater, Fla.

[73] Assignee: R. P. Scherer Corporation, Troy, Mich.

[21] Appl. No.: 549,998

[22] Filed: Nov. 8, 1983

Related U.S. Application Data

[62] Division of Ser. No. 376,115, May 7, 1982, Pat. No. 4,428,927.

[51] Int. Cl.$^3$ .................. A23G 3/30; A61K 9/68; A61K 9/48
[52] U.S. Cl. ...................... 424/48; 424/37; 426/3; 426/5; 264/4; 514/962; 514/774
[58] Field of Search ............... 424/48, 37, 360; 426/3, 426/5; 264/4

[56] References Cited

U.S. PATENT DOCUMENTS

| | | | |
|---|---|---|---|
| 810,210 | 1/1906 | Laws | 426/5 |
| 2,203,436 | 6/1940 | Kurtess | 426/3 |
| 2,331,572 | 10/1943 | Scherer | 264/4 |
| 2,332,671 | 10/1943 | Scherer | 264/4 |
| 2,580,683 | 1/1952 | Kreuger | 424/37 |
| 2,886,440 | 5/1959 | Kramer et al. | 426/5 |
| 2,886,441 | 5/1959 | Kramer et al. | 426/5 |
| 2,886,442 | 5/1959 | Kramer et al. | 426/5 |
| 2,886,446 | 5/1959 | Kramer et al. | 426/5 |
| 2,886,447 | 5/1959 | Kramer et al. | 426/5 |
| 2,886,448 | 5/1959 | Kramer et al. | 426/5 |
| 2,886,449 | 5/1959 | Kramer et al. | 426/5 |
| 3,255,018 | 6/1966 | Comollo | 426/4 |
| 3,422,184 | 1/1969 | Goldman et al. | 424/48 |
| 3,515,781 | 6/1970 | Steinberg | 424/37 |
| 3,857,963 | 12/1974 | Graff et al. | 426/5 |
| 3,894,154 | 7/1975 | Graff et al. | 426/5 |
| 4,156,740 | 5/1979 | Glass et al. | 426/3 |
| 4,157,402 | 6/1979 | Ogawa et al. | 426/5 |
| 4,161,544 | 7/1979 | Kaul | 426/5 |
| 4,196,189 | 4/1980 | Raaf et al. | 424/37 |
| 4,238,475 | 12/1980 | Witzol et al. | 424/48 |
| 4,241,091 | 12/1980 | Stroz et al. | 426/4 |
| 4,250,196 | 2/1981 | Friello | 426/5 |
| 4,252,829 | 2/1981 | Vazzl | 426/5 |
| 4,292,329 | 9/1981 | Ogawa et al. | 426/5 |

FOREIGN PATENT DOCUMENTS

| | | | |
|---|---|---|---|
| 477005 | 9/1951 | Canada | 426/3 |
| 2077913 | 5/1971 | France | 424/21 |
| 51-79763 | 12/1976 | Japan | 426/3 |
| 1060258 | 3/1967 | United Kingdom | 424/37 |

*Primary Examiner*—Shep K. Rose
*Attorney, Agent, or Firm*—Allegretti, Newitt, Witcoff & McAndrews, Ltd.

[57] ABSTRACT

A chewable, filled, one-piece soft elastic gelatin (SEG) capsule. The capsule includes a shell which is formed from a formulation of gelatin, water, a plasticizer, and a masticatory substance. The masticatory substance is present in the shell in an amount of about 1–75 percent by weight and the gelatin is present in the shell in an amount of about 10–90 percent by weight. A fill material is contained within the shell. The fill may be selected from a variety of materials, including candy, various confectionaries, antacids, cough and cold preparations, sore throat remedies, antiseptics, dental preparations, such as fluorides, breath fresheners, and the like. In manufacturing the SEG capsules, a molten gel mass is prepared with a dispersion of a molten masticatory substance therein. A suitable fill material is also prepared. The gelatin formulation containing the masticatory substance dispersed therein is formed as a shell around the fill material. The capsules are dried until the desired chewing characteristics are attained.

9 Claims, No Drawings

MASTICATORY SOFT ELASTIC GELATIN CAPSULES AND METHOD FOR THE MANUFACTURE THEREOF

REFERENCE TO RELATED APPLICATION

This is a division of application Ser. No. 376,115, filed May. 7, 1982, now U.S. Pat. No. 4,428,927.

BACKGROUND OF THE INVENTION

Field of the Invention and Description of the Prior Art

This invention relates to a unique gelatin capsule formulation and a method for its manufacture and it particularly relates to a soft elastic gelatin capsule (SEG) formulation, usually containing a fill material, wherein the formulation may be chewed in the mouth over an extended period of time.

Filled, one-piece, SEG capsules have been widely known and used for many years for a variety of purposes. These SEG capsules have properties which are quite different from two-piece telescoping hard shell capsules. The SEG capsules usually have a fill material, which is normally a liquid. The fill may be any of a variety of materials, such as industrial or cosmetic, non-consumable products, such as bath oils and adhesives. More commonly, SEG capsules are used to encapsulate consumable materials such as vitamins and pharmaceuticals. With reference to the application of William R. Ebert, et al., dated Oct. 24, 1980, Ser. No. 200,475, (now abandoned) there is disclosed a method and capsule, having no added masticatory substance, wherein the characteristic and sometimes unpleasant flavor of gelatin is masked with maltol or ethyl malthol. The avoidance of an unpleasant taste is particularly important when the capsule shell is chewed or otherwise broken in the oral cavity in order to release the fill. This is the case, for example, with a chewable cough, antacid, analgesic, or candy type of product.

With respect to providing a chewable, SEG capsule product, there is generally a significant problem because the SEG capsule generally dissolves rapidly in the mouth, thereby leaving little or no residue for further chewing. A chewable SEG capsule product should not only be non-toxic, but it should also be of a suitable size and leave a chewable, insoluble residue in the mouth and this residue should not change significantly in size upon continued chewing; at all times, the insoluble residue should retain a generally normal chewing texture or consistency. In addition, it has generally been considered a problem to prepare a SEG capsule containing an insoluble masticatory substance because the masticatory substance and the gelatin shell formulation itself are not considered to be compatible when using conventional formulations and SEG capsule manufacturing techniques.

SUMMARY OF THE INVENTION

It is therefore an important object of the present invention to provide a chewable, filled, one-piece, SEG capsule and a process for its manufacture wherein an insoluble masticatory substance is contained within the shell.

It is another object of the present invention to provide a SEG capsule containing a masticatory substance wherein upon chewing of the capsule in the mouth, the size of the chewable residue does not change significantly and the insoluble residue retains a normal chewing consistency over an extended period of time.

It is also an object of the present invention to provide a unique method for manfacturing a chewable SEG capsule wherein the method involves dispersing a molten masticatory substance within a molten gel mass.

It is a further object of the present invention to provide an improved chewable SEG capsule containing a fill wherein the process is characterized by its compatibility with known SEG capsule manufacturing techniques, such as the rotary die process.

Further purposes and objects of the present invention will appear as the specification proceeds.

The foregoing objects are accomplished by providing a chewable, filled, one-piece SEG capsule wherein a molten gel shell formulation is formed from gelatin, water, a plasticizer, and a synthetic or natural masticatory substance. The masticatory substance, while in a molten state, is dispersed within the gel formulation, also while in the molten state. The dispersion is thoroughly mixed. Gelatin is present in the formulation in an amount of about 10–90 percent by weight and the masticatory substance is present in the shell in an amount of about 1–75 percent by weight. A fill material is formed and encapsulated within the shell. After encapsulation, the shell is dried until the SEG capsule acquires the desired chewing texture and characteristics.

DETAILED DESCRIPTION OF THE PREFERRED EMBODIMENTS

Generally speaking, the present invention relates to an improved, chewable, filled, one-piece, seamless SEG capsule. The improvement is specifically directed to the formulation and manufacturing technique which results in compatibility between an insoluble masticatory substance and gelatin normally used in the SEG capsule shell. Generally speaking, the insoluble masticatory substance is present in the gelatin shell in an amount of about 1–75% by weight while the gelatin is present therein in an amount of about 10–90% by weight. The present invention is specifically directed to a SEG capsule containing a fill, usually a liquid fill, wherein the gel is heat sealable and therefore capable of being manufactured on conventional rotary die encapsulation equipment.

In making the gel preparation for the shell, a molten gel mass is also prepared and a molten masticatory substance is dispersed in the gel mass. A fill material is prepared and the shell comprising the gel mass, with the masticatory substance dispersed therein, is formed as a shell around the fill material. Finally, the shell is dried until the desired chewable texture is obtained for the gel shell containing the masticatory substance.

In a preferred form of our capsule, the gelatin capsule, made in accordance with the invention, comprises about 1–75% by weight of a known insoluble masticatory substance, about 10–90% by weight gelatin, about 1–30% by weight of a plasticizer, such as glycerine or sorbitol, about 5–40% by weight of water, and about 0–10% taste modifiers or other additives. In addition, the gelatin shell will commonly contain a preservative, such as mixed parabens, ordinarily methyl or propyl parabens in about a 4:1 weight ratio. The parabens are incorporated in the shell formulation in minor proportions as compared to the total weight of the shell formulation. Conventional SEG capsules utilizing gelatin have a bloom value of about 150–200, although this value may be varied.

Suitable insoluble masticatory substances utilized in our invention may be found upon reference to Federal Regulations, Title 21, Section 172.615 which lists various natural and synthetic masticatory substances which may be used alone or in a variety of combinations. The natural masticatory substances (coagulated or concentrated lattices) of vegetable origin are as follows: Chicle, Chiquibul, Crown gum, Gutta hang kang, Massaranduba balata (and the solvent-free resin extract of Massaranduba balata), Massaranduba chocolate, Nispero, Rosidinha (rosadinha), Venezuelan chicle, Jelutong, Leche caspi (sorva), Pendare, Perillo, Leche de vaca, Niger gutta, Tunu (tuno), Chite, and Natural rubber (smoked sheet and latex Hevea brasiliensis solids).

Suitable synthetic masticatory substances includes: Butadiene-styrene rubber, isobutylene-isoprene copolymer (butyl rubber), paraffin, petroleum wax, petroleum wax synthetic, polyethylene (mol. wt. 2,000–21,000), polyisobutylene (mol. wt. 37,000), polyvinyl acetate (mol. wt. 2,000) and polyvinyl alcohol (not listed in Fed. Reg.)

In the manufacturing of the chewable SEG capsules, in order to attain the desired characteristics, that is, the desired chewing characteristics, it is important that the molten masticatory substance is dispersed in the molten gel mass. Generally speaking, this dispersion of the masticatory substance in the molten gel mass is accomplished in any of a variety of ways. First, all of the ingredients, including the masticatory substance and the gel mass, are mixed together and all the ingredients are heated until melted. The masticatory substance is then dispersed by thorough mixing, generally in a vacuum atmosphere, by use of a suitable mixer commonly used for preparing a molten gelatin mass for a SEG capsule shell.

In a second method, a molten gel mass is prepared by mixing the ingredients (including, for example, gelatin, glycerine, and water) and mixing until the molten gel mass is formed. Suitable vehicles for the gel mass are glycerin, sorbital, water, glucose, fructose, acacia, and mannitol. Thereafter, the masticatory substance is added to the molten gel mass and the entire mixture is then heated to above the melting point of the masticatory substance, which is dependent upon the particular masticatory substance or substances that are used. The masticatory substance is then dispersed in the molten gel mass by mixing.

Another method of preparing the dispersion of a molten masticatory substance in the molten gel mass is to prepare the molten gel mass, as described above, add a molten masticatory substance which has been previously melted, and finally, dispersing the molten masticatory substance in the molten gel mass through thorough mixing. An important aspect of the method is appropriate mixing in order to prepare the dispersion of the molten masticatory substance in the molten gel mass, which result is accomplished in a variety of ways. In each of the above methods, any suitable flavorings or taste modifiers are added to the dispersion.

By following the above method for making the masticatory gel mass, with the above relative proportions between the materials making up the gel-masticatory substance mass, a desired gel, having unique properties including thermal plasticity, gel forming ability, heat sealability, reduced hydrophilic properties, ease of drying, and desired chewing characteristics, results.

A suitable fill material is prepared separately. Suitable fill materials include candy, confectionaries, antacids, cough preparations, cold preparations, sore throat remedies, antiseptics, dental preparations including fluorides, breath fresheners and the like. The preparation of the fill material may be accomplished in a wide variety of ways. The fluid material must be compatible with the gel shell and must not break down the shell during a period of normal storage. This problem is well known and is solved in a variety of ways known to those skilled in the art. Suitable vehicles for the fill are neutral oil, mineral oil, water, ethyl alcohol, vegetable oil, and fructose syrup. As with the gel mass, a suitable flavoring or taste modifier is preferably added to the fill.

Suitable taste modifiers or flavorings are used in the fill composition, the gelatin composition, or in both simultaneously. The particular taste modifier and/or flavor that is used may vary widely. Similarly, the proportions between various taste modifiers and/or flavors vary widely according to the taste desired. The taste modifiers and/or flavorings may be desirably selected from the following: cherry syrup, citric acid, dextrose, essential oil (i.e., clove, lemon, orange, peppermint, spearmint), ethyl vanillin, glucose, honey, mannitol, methyl salicylate, raspberry syrup, saccharin, saccharin sodium, sorbital, sucrose, wild cherry syrup, and mixtures thereof.

The present capsules are simultaneously formed and filled with a fill material, using conventional method and apparatus, such as those using rotary die process, as disclosed, for example, in U.S. Pat. Nos. 1,970,396; 2,288,327; and 2,318,718. Such equipment is commercially used, for example, by R. P. Scherer Corporation and utilizes the said rotary die process for encapsulating various fill materials in a gel mass.

The SEG chewable gelatin capsules are formed into any desired shape, color and size which is to be of such size as to be readily received and chewed in the mouth. Finally, the formed and filled capsules are dried for a suitable length of time in order that the desired chewing characteristics may be attained. The particular length of time for the drying to occur may vary over a wide range.

The following examples set forth useful SEG capsule shell formulations and various fill materials embodying the present invention:

EXAMPLE I

| Composition of Gel Mass in % by weight | |
| --- | --- |
| Synthetic masticatory substances | 29 |
| Gelatin, Type HB | 27 |
| Glycerine | 15 |
| Water | 24 |
| Taste modifiers and others (Mixture of powdered sugar, saccharin, mono-sodium glutamate, sodium chloride, furaneol, and peppermint oil) | 5 |

Mix gelatin, glycerin and water into a fluff and heat until molten. Add the synthetic masticatory substances and heat until molten (above melting point). (In this formulation, the synthetic mastic used is sold under the trademarks PALOSA or DREYCO and is available from Dreyfus Company of South Plainfield, N.J.) Disperse the molten gum in the gel with a suitable mixer. Add taste modifiers and other additives and mix well. Keep gel mass at a constant temperature of 60° C. until ready for use in encapsulation.

| Composition of Fill Material in mg/capsule | |
| --- | --- |
| Dried Aluminum hydroxide gel, USP | 282 |
| Magnesium hydroxide, NF | 85 |
| Simethicone, NF | 25 |
| Suspending agents (Octaglyceryl monostearate and octaglyceryl monooleate) | 125 |
| Vehicle (Neutral Oil) | 378 |
| Taste modifiers and others (Powdered sugar, saccharin, mono-sodium glutamate, sodium chloride, furaneol, peppermint oil, and citric acid) | 505 |
| Fill wt., mg. | 1400 |

Mix suspending agents with vehicle and simethicone. Add dried aluminum hydroxide gel and magnesium hydroxide and mix well. Add taste modifiers and other additives and mix into a smooth suspension and deaerate the mixture.

Encapsulate fill material with the gel mass as prepared above on Scherer rotary machine or other similar machine using the appropriate size and shape die. Dry the freshly prepared SEG capsules to the specified consistency in drying chambers.

EXAMPLE II

| Composition of Gel Mass in % by weight | |
| --- | --- |
| Natural masticatory substances (Mexican Chicle) | 25 |
| Gelatin, Type HB | 24 |
| Glycerin | 11 |
| Water | 37 |
| Taste Modifiers and others (Peppermint oil, saccharin, mono-sodium glutamate, sodium chloride, furaneol and anethole) | 3 |

Mix gelatin, glycerin and water into a fluff. Add natural masticatory substances and heat until molten. Disperse molten natural gum with a suitable mixer. Add taste modifiers and other additives and mix well. Keep molten gel mass at a constant 60° C. temperature until encapsulation.

| Composition of Fill Material in mg/capsule | |
| --- | --- |
| Dextromethorphan HBr 10% adsorbate | 150 |
| Benzocaine | 3 |
| Suspending agents (Beeswax and lecithin) | 64 |
| Vehicle (Soybean oil) | 403 |
| Taste modifiers and others (Powered sugar, methanol, anethole) | 347 |
| Fill Wt., mg. | 967 |

Mix suspending agents with vehicle. Add dextromethorphan HBr 10% adsorbate and benzocaine and mix well. Add taste modifiers and other additives and mix into a smooth suspension, and deaerate the mixture.

Encapsulate the fill material with the above prepared gel mass on Scherer rotary machine or other similar machines using a die of the appropriate size and shape. Dry the freshly prepared SEG capsules to the specified consistency in drying chambers.

EXAMPLE III

| Composition of Gel Mass in % by weight | |
| --- | --- |
| Chicle | 28 |
| Gelatin, Type HB | 28 |
| Glycerin | 11 |
| Water | 28 |
| Taste modifiers and others (Furaneol, orange flavor, saccharin, mono-sodium glutamate, sodium chloride, citric acid) | 5 |

Prepare gel fluff by mixing gelatin, glycerin and water. Melt gel fluff and chicle separately. Add molten chicle to molten gel mass and disperse thoroughly with a suitable mixer. Add taste modifiers and other additives and mix well. Keep molten gel at a constant 60° C. temperature until encapsulation.

| Composition of Fill Material in mg/capsule | |
| --- | --- |
| Brand of fructose corn syrup | 3088 |
| Flavors (Orange flavoring) | 2 |
| Fill wt., mg. | 3090 |

Add flavors to brand of fructose corn syrup and mix well. Deaerate any trapped air before encapsulation.

Encapsulate fill material with the above prepared gel mass on Scherer rotary machines or other similar machine using a die of the appropriate size and a round shape. Dry the freshly prepared SEG capsules to the specified consistency in drying chambers.

EXAMPLE IV

Chewable Sore Throat Capsules

| Composition of Gel Mass in % by weight | |
| --- | --- |
| Chicle | 14 |
| Synthetic masticatory substances (Dreyco) | 15 |
| Gelatin, Type HB | 27 |
| Glycerin | 15 |
| Water | 24 |
| Taste modifiers and other* (Saccharin, methyl salicylate) | 5 |

*Each capsule shell to contain 8 mg. benzocaine

Prepare gel fluff by mixing gelatin, glycerin and water. Add both masticatory substances and heat until molten. Disperse molten gums thoroughly with suitable mixer. Add taste modifiers and other additives and mix well. Keep the molten gel mass at a constant 60° C. temperature until encapsulation.

| Composition of Fill Material in mg/capsule | |
| --- | --- |
| Acetaminophen, USP | 650 |
| Suspending Agents (Beeswax and lecithin mixture) | 206 |
| Vehicle | 808 |
| Taste modifiers and others (Powdered sugar and saccharin) | 1044 |
| Flavors (Menthol, methyl salicylate, oil of wintergreen) | 137 |
| Fill wt., mg. | 2845 |

Mix the suspending agents with the vehicle. Add acetaminophen and mix well. Add taste modifiers and flavors and mix well. Mill mix if necessary. Deaerate before encapsulation.

Encapsulate the fill material with the above prepared gel mass on a Scherer rotary machines or other similar machine using a die of the appropriate size and shape. Dry the freshly prepared SEG capsules to the specified consistency in drying chambers.

EXAMPLE V

Breath Freshener Capsules

| Composition of Gel Mass | |
|---|---|
| Gelatin | 28.326% w/w |
| Water | 25.234% w/w |
| Glycerin | 15.758% w/w |
| Saccharin | 0.001% w/w |
| Methyl salicylate | 0.002% w/w |
| DREYCO base gum | 30.420% w/w |

Prepare gel by mixing gelatin, glycerin and water. Add the gum and heat until molten. Disperse gum throughout with mixing. Add saccharin and methyl salicylate and mix. Maintain gel mass at 60° C. until encapsulation.

| Composition of Fill | |
|---|---|
| Neutral Oil | 93.144% w/w |
| Menthal U.S.P. | 2.257% w/w |
| Methyl salicylate | 4.513% w/w |
| Saccharin | 0.001% w/w |

Mix ingredients and deaerate before encapsulation.

Encapsulate the fill in the gel mass on a Scherer rotary die machine using a die of appropriate size and shape. Dry the capsules in a drying chamber.

While in the foregoing there has been provided detailed descriptions of preferred embodiments of the present invention, it is to be understood that all equivalents obvious to those having skill in the art are to be included within the scope of the invention as claimed.

What we claim and desire to secure by Letter Patent is:

1. A method for preparing a chewable, non-toxic, filled, soft elastic gelatin capsule having selected chewable texture following chewing thereof, said method comprising the steps of preparing a soluble molten component of gelatin, water and a plasticizer selected from the group consisting of glycerin and sorbitol, preparing an insoluble molten masticatory substance, dispersing said insoluble substance in said soluble molten component for forming a gelatin shell formulation for said gelatin capsule, preparing a fill material, forming a shell from said gelatin shell formulation around said fill material to form said capsule, drying said shell, said selected chewable texture being attained when an insoluble chewable residue is formed from said insoluble substance upon chewing of said capsule, said residue substantially retaining its size and chewing consistency during chewing, the relative proportions of said soluble compoent and said insoluble masticatory substance being such that the size and chewing characteristics of said chewable residue are attained.

2. The method of claim 1 wherein said masticatory substance is chicle.

3. The method of claim 1 wherein said insoluble component and said soluble masticatory substance component cooperate to form a gel mass used to form said gelatin shell, said gel mass comprising about 14–30 percent by weight of said masticatory substance, about 24–28 percent by weight of gelatin, about 11–16 percent by weight of glycerin and about 24–37 percent by weight of water.

4. The method of claim 1 wherein said fill material comprises flavored corn syrup.

5. The method of claim 1 wherein said plasticizer is present in said shell formulation in an amount of about 12–30 percent by weight and said water is present in said shell in an amount of about 5–40 percent by weight.

6. The method of claim 1 wherein said masticatory substance comprises a natural masticatory substance selected from the group consisting of Chicle, Chiquibul, Crown gum, Gutta hang kang, Massaranduba balata, Massaranduba chocolate, Nispero, Rosidinha, Venezuelan chicle, Jelutong, Leche caspi, Pendare, Perillo, Leche de vac, Niger gutta, Tunu, Chite, or Natural rubber.

7. The method of claim 1 wherein said soluble molten component and said insoluble masticatory substance are mixed together and heated until molten and thereafter said masticatory substance is dispersed in said insoluble component.

8. The method of claim 1 wherein said soluble molten component is first formed, said insoluble masticatory substance is added to said soluble molten component, to form a mixture and the entire mixture is heated to a temperature about the melting point of the masticatory substance and thereafter the masticatory substance is dispersed in the molten component.

9. The method of claim 1 wherein said soluble molten component is prepared, said insoluble molten masticatory substance is prepared, said insoluble molten masticatory substance is added to said soluble component and dispersed in said molten component.

* * * * *